United States Patent [19]

Tanaka et al.

[11] Patent Number: 5,291,021
[45] Date of Patent: Mar. 1, 1994

[54] POSITRON COMPUTED TOMOGRAPHY SCANNER

[75] Inventors: Eiichi Tanaka; Nakahiro Satoh; Keiji Shimizu, all of Hamamatsu, Japan

[73] Assignee: Hamamatsu Photonics K.K., Hamamatsu, Japan

[21] Appl. No.: 906,858

[22] Filed: Jun. 30, 1992

[30] Foreign Application Priority Data

Jul. 1, 1991 [JP] Japan .................................. 3-160647

[51] Int. Cl.⁵ .............................................. G01T 1/166
[52] U.S. Cl. .................... 250/363.03; 250/363.10; 250/505.1; 250/363.04
[58] Field of Search .................. 250/363.10, 363.03, 250/363.04, 505.1

[56] References Cited

U.S. PATENT DOCUMENTS

| | | | |
|---|---|---|---|
| 4,259,578 | 3/1981 | Thompson | 250/363.03 |
| 4,403,338 | 9/1983 | Rudin et al. | 378/146 |
| 4,837,439 | 6/1989 | Genna et al. | 250/363.04 |

FOREIGN PATENT DOCUMENTS

| | | |
|---|---|---|
| 141135 | 5/1985 | European Pat. Off. . |
| 2949946 | 6/1981 | Fed. Rep. of Germany . |
| 56-163468 | 12/1981 | Japan . |
| 57-149980 | 9/1982 | Japan . |

OTHER PUBLICATIONS

"The Effect of Collimation on Singles Rates in Multi-Slice Pet", Thompson, C. J., IEEE Transactions on Nuclear Science, vol. 36, No. 1, Feb. 1989, pp. 1072–1077.

*Primary Examiner*—Carolyn E. Fields
*Attorney, Agent, or Firm*—Cushman, Darby & Cushman

[57] ABSTRACT

A positron CT scanner includes a plurality of detectors arranged in a generally cylindrical multi-layers of rings, and slice septa for restricting visual fields of the detectors so that the visual fields intersect a set axis. An interval of the slice septa is substantially corresponds to a plural number of detector cells each of which can determine positions of γ rays incident in the direction of the set axis. The slice septa are movable relatively to the detector cells in the direction of the set axis during a γ ray counting operation.

53 Claims, 18 Drawing Sheets

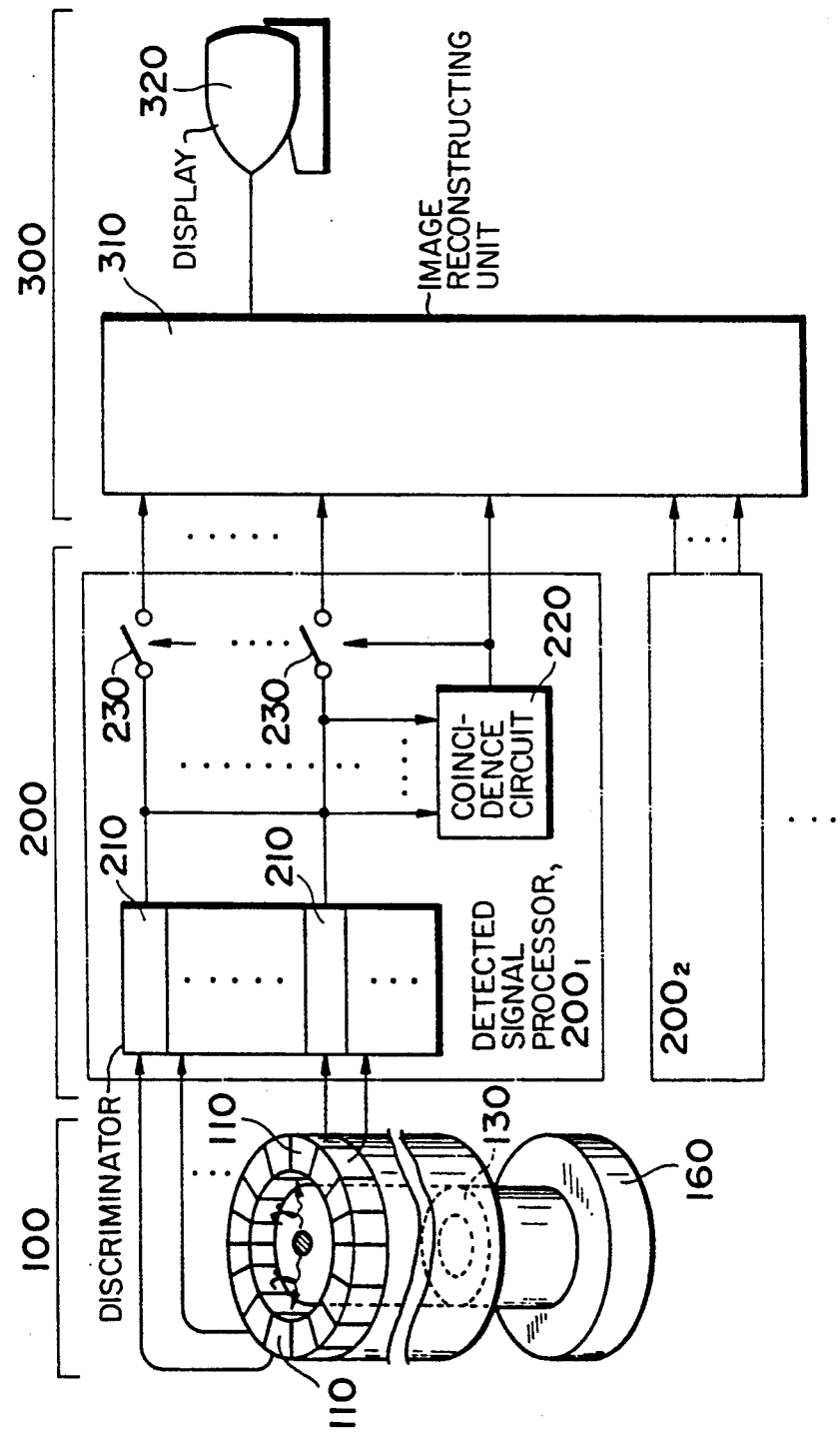

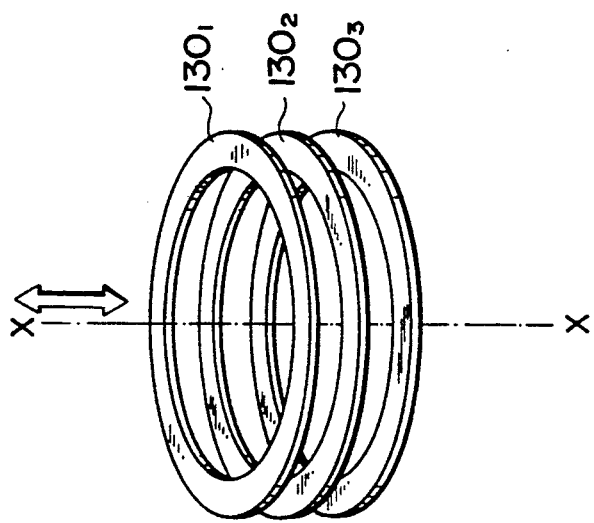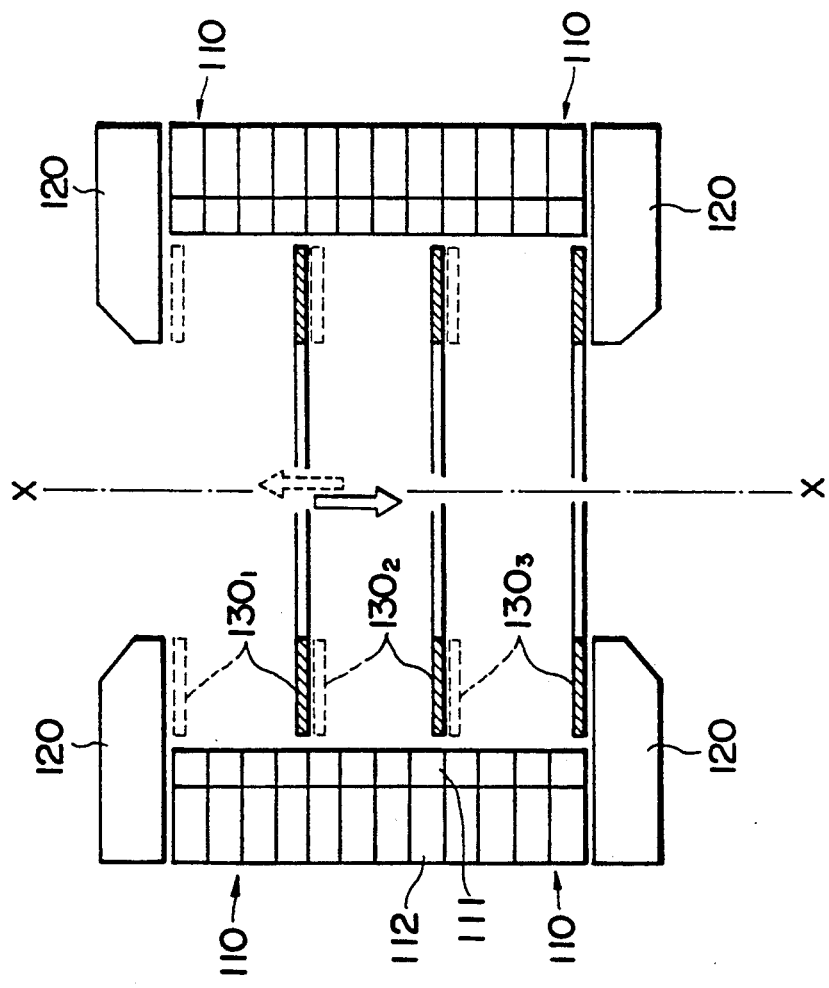

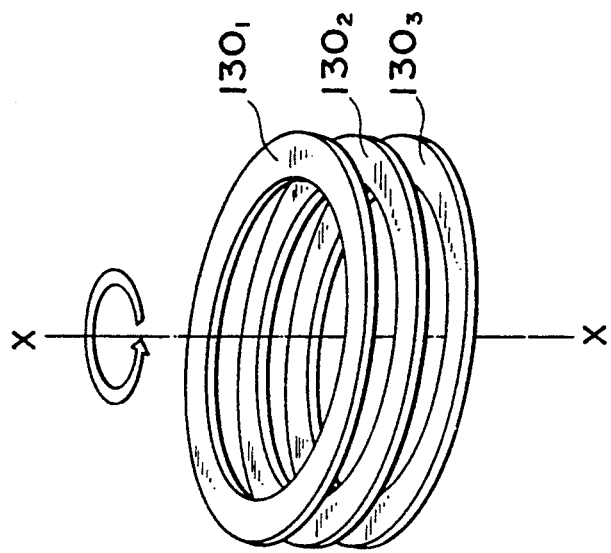
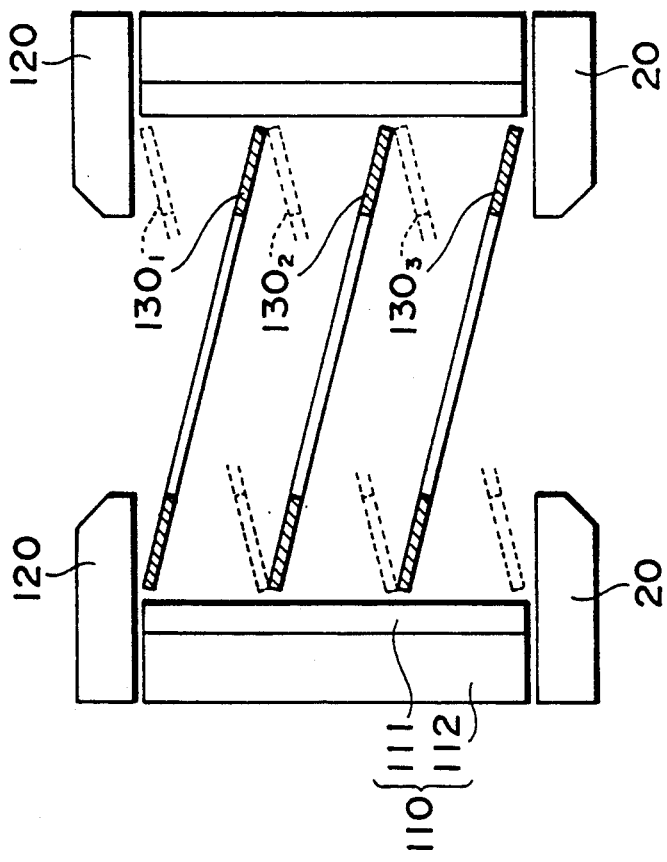

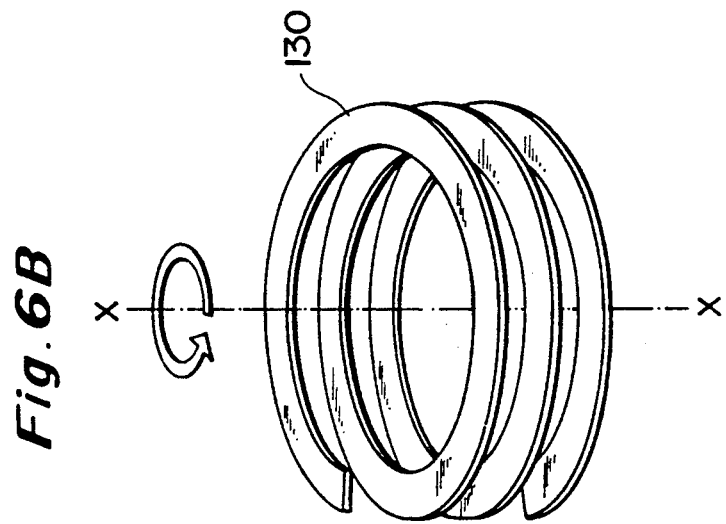
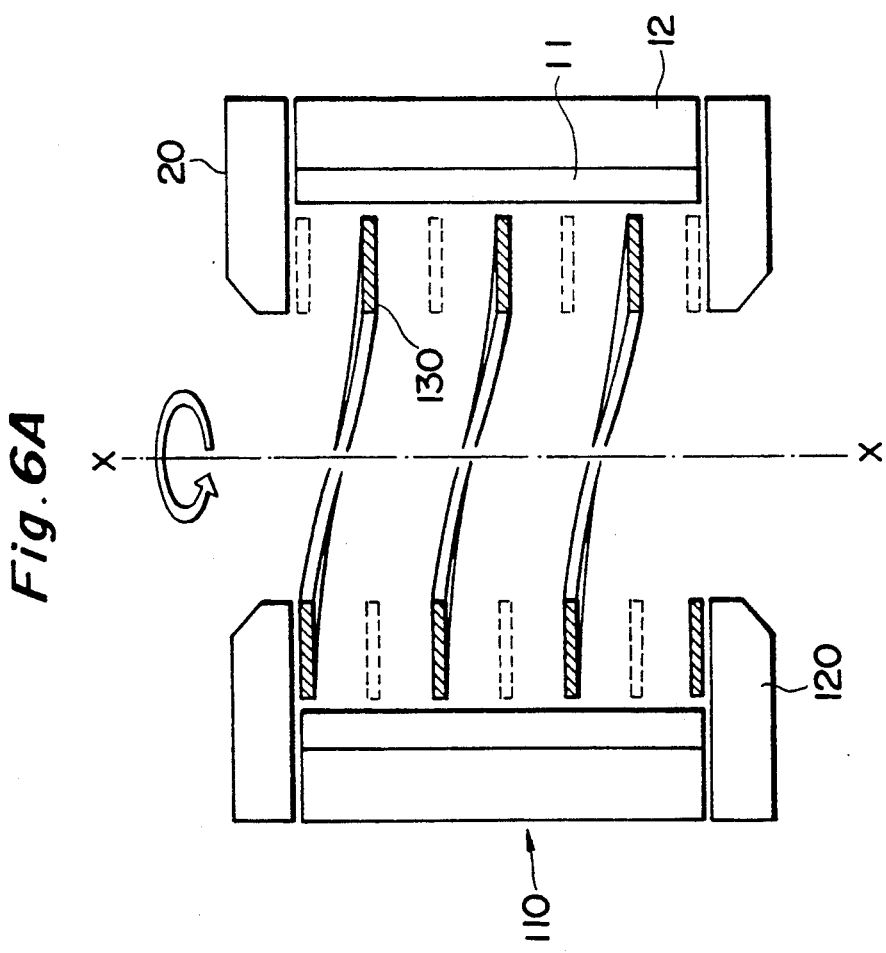

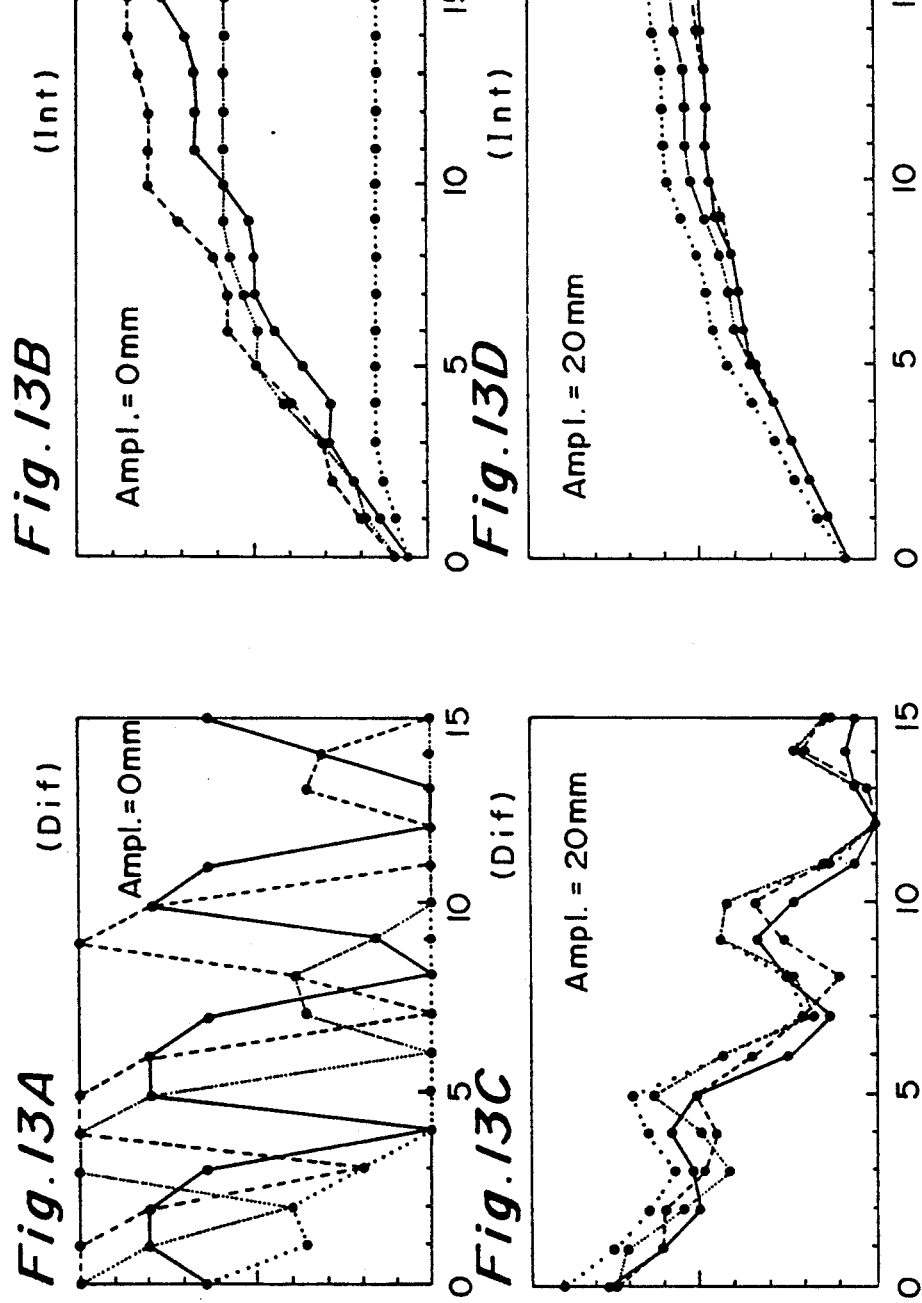

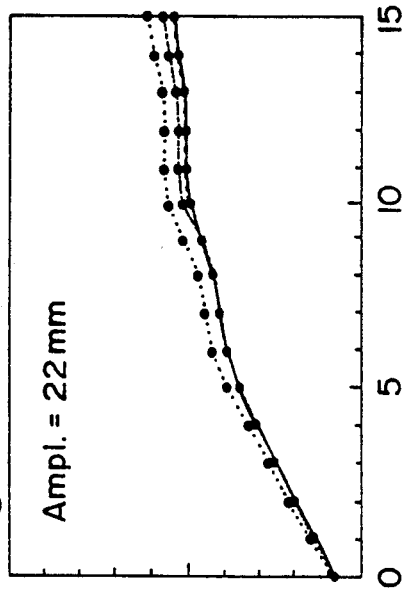
Fig.14B Ampl.=22mm
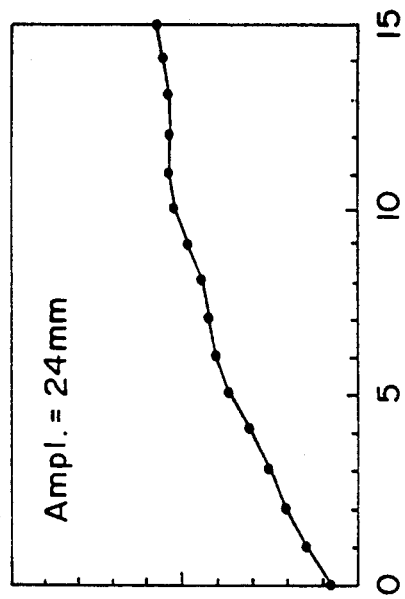
Fig.14D Ampl.=24mm
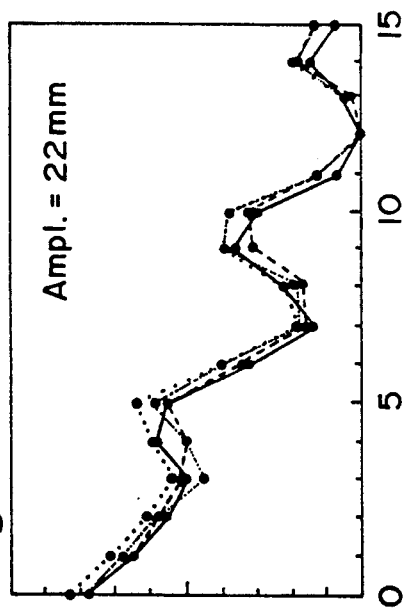
Fig.14A Ampl.=22mm
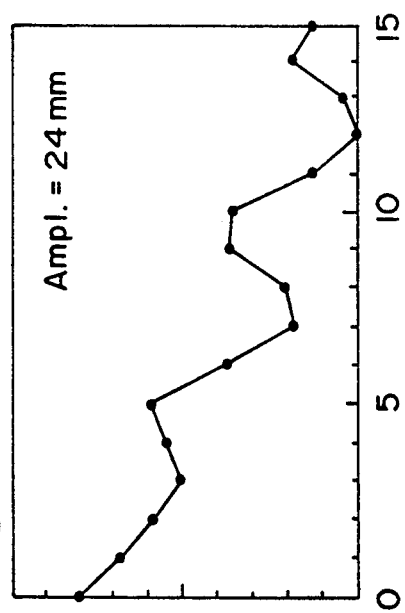
Fig.14C Ampl.=24mm

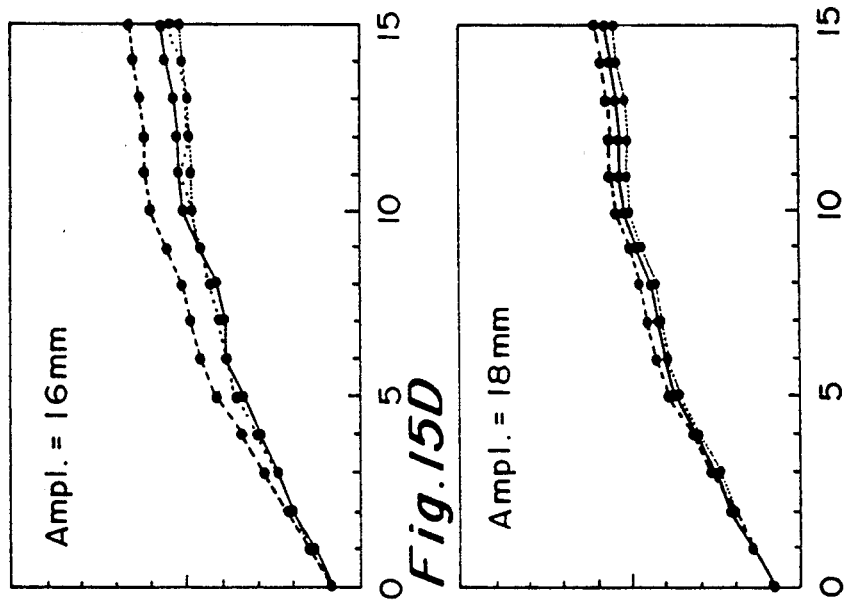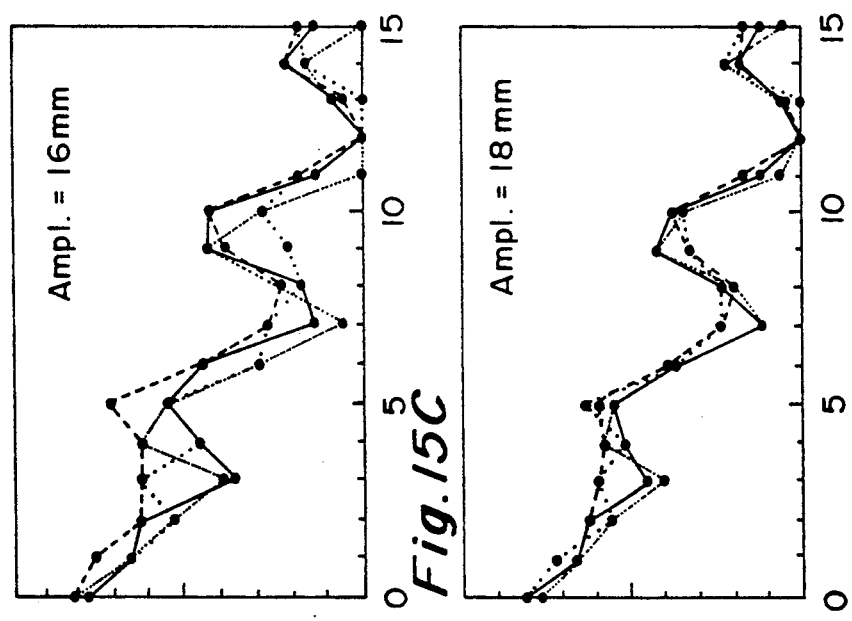

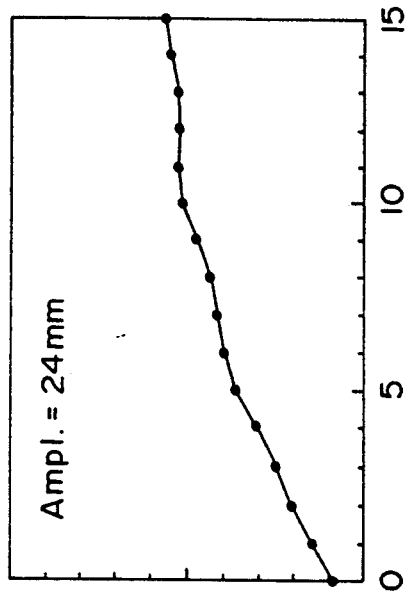
Fig. 17A  Ampl. = 24mm
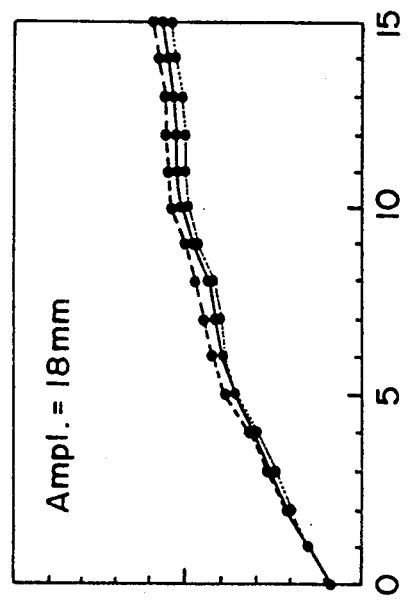
Fig. 17B  Ampl. = 24mm
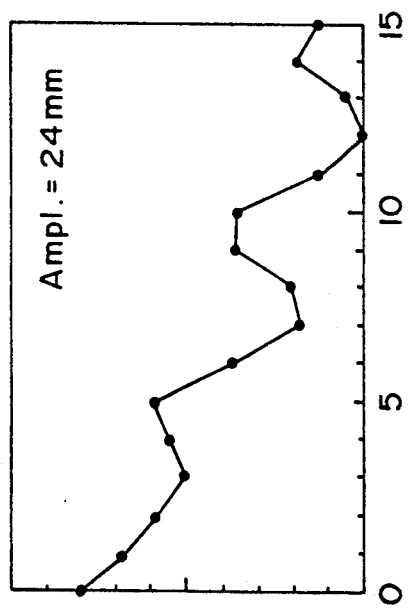
Fig. 17C  Ampl. = 18mm
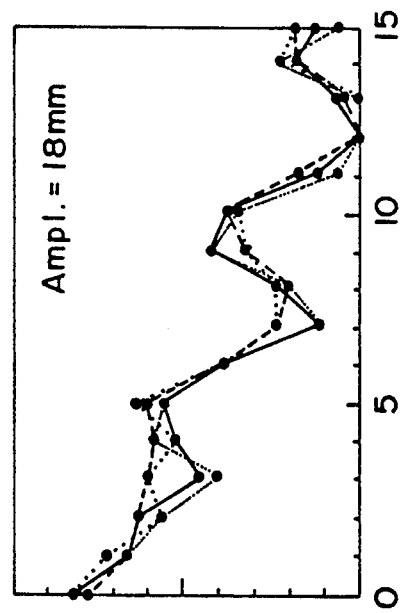
Fig. 17D  Ampl. = 18mm Ampl. = 22mm Ampl. = 22mm Ampl. = 24mm Ampl. = 24mm

POSITRON COMPUTED TOMOGRAPHY SCANNER

BACKGROUND OF THE INVENTION

This invention relates to a positron computed tomography (CT) scanner.

Positron CT scanners, also referred to as PET (Positron Emission Tomography) are known (S. E. Drenzo et., IEEE Trans. Nucl. Sci., NS-26, No. 2: 2790-2793, 1979, etc.). These devices are used for dosing medicines to patients, and such medicines are labelled by radioactive isotopes to image their internal distributions in the patients. In such PET, a number of $\gamma$ (gamma) ray detectors are arranged in rings for the detection by coincidence counting of a pair of annihilating photons (0.51 MeV) emitted in directions opposite to each other by the pair annihilation of a positron and an electron. Multi-layers of detector rings are provided, and an intra-ring image can be formed by means of the coincidence counting of the detectors belonging to one ring, while an inter-ring image can be obtained by means of the coincidence counting of adjacent ones of the rings. Accordingly, a PET scanner having j layers of detector rings can provide tomographic images of $2j-1$ layers at once. A slice septum (collimator) is provided between one of the detector rings and its adjacent one for shielding unnecessary $\gamma$ rays and internal scattered $\gamma$ rays, whereby unnecessary counting by the detectors is decreased to reduce counting losses and accidental coincidences. The resolving power is determined mostly by an area of a photon incident surface of a detector (BGO scintillator). The sectional resolving power of the current devices has reached 3-5 mm (full width at half maximum value).

FIG. 1 is a schematic sectional view of a conventional PET scanner. Each $\gamma$ ray detector 110 includes both a scintillator 111 and a photomultiplier 112 and these detectors are arranged in rings laid one above another, and shield collimators 120 are provided above the top ring and below the bottom ring. The central axis of the rings is shown as X in FIG. 1. Slice septa 130 are arranged so as to restrict the detection fields of the $\gamma$ ray detectors 110 vertically to the central axis. Generally one slice septum 130 is provided per one layer of $\gamma$ ray detectors 110. The $\gamma$ ray shielding effect of the slice septa 130 can reduce noise components as described above.

That is, in the case of coincidence counting by two $\gamma$ ray detectors 110, as shown in FIG. 1, a pair of $\gamma$ rays from one radioisotope 141 are incident on the $\gamma$ ray detectors $110_1$, $110_2$; $\gamma$ rays from two radioisotopes 142, 143 are concurrently incident by accident on the $\gamma$ ray detectors $110_3$, $110_4$; or one of a pair of $\gamma$ rays from one radioisotope 144 being detected by the $\gamma$ ray detector $110_6$, the other of the $\gamma$ rays being scattered by a scatterer 150 and detected by the $\gamma$ ray detector $110_5$. All the coincidences other than those of the $\gamma$ rays from the radioisotope 141 are noise. The slice septa 130 for shielding $\gamma$ rays restrict the detection fields of the $\gamma$ ray detectors 110 to reduce such noise components.

But as the respective $\gamma$ ray detectors 110 are increasingly more miniaturized to make an interval between each of the slice septa 130 and its adjacent one narrower for the improvement of a resolving power, the $\gamma$ ray detecting efficiency is lowered proportionally to a square of an interval between the slice septa 130. Accordingly it tends to take much more time for counting to form a sufficiently precise image. As a countermeasure to this, so-called three-dimensional PET has been recently studied. In the three-dimensional PET, no slice septa are provided to count not only intra-coincidences of respective detector rings and inter-coincidences between adjacent ones of the detector rings, but also coincidences between ones of the detector rings remote from each other are counted to obtain images at respective slices to restore an image.

However, such three-dimensional PET, which acquires and processes three-dimensional data, has a disadvantage of the above-mentioned quite high noise because slice septa are not used. In the case such three-dimensional PET including the conventional slice septa provided between detector rings is realized, the numerical aperture of the $\gamma$ ray detectors 110 is comparatively large, and inevitably the slice septa 130 have to be thinned and small-sized. Then the $\gamma$ ray shielding effect of the slice septa 130 is lowered with the result that the above-mentioned accidental coincidences and scattered coincidences are adversely acquired in data, and sharp image cannot be obtained.

SUMMARY OF THE INVENTION

This invention has been made to solve the above-described problems. An object of this invention is to provide a positron CT scanner which can effectively remove noise in the case that position resolving power of the detectors are improved to raise a resolving power, and in the case that three-dimensional data acquisition and processing are performed.

That is, an object of this invention is to provide a positron CT scanner comprising a plurality of detectors (e.g., BGO scintillators and photomultipliers) each having one detection cell or a plurality of detection cells for detecting incident photons and arranged in multi-layers rings of which a central axis is a predetermined axis; slice septa for restricting detection fields of the detectors so that the detection fields cross the predetermined axis, the slice septa spacing the detectors from each other in the direction of the axis at an interval a total of which substantially corresponds to a total of a size of the detection cells in the direction of the predetermined axis; means for driving the slice septa (e.g., in piston-type reciprocating motions and rotary motions); means for pre-processing outputs of associated ones of the detectors and selecting two photons generated by a pair annihilation of a positron and an electron (e.g., discriminators, coincidence circuits, and switches); and means for restoring a sectional material distribution of a detected sample (e.g., a computer system and an image display). The slice septa are moved during a counting operation of photons.

In order to make the slice septa relatively movable for the detectors, the slice septa themselves are movable in the direction of the predetermined axis, or are able to perform precessions. Otherwise, positions of the slice septa may be changed continuously or by steps in the direction of the predetermined axis, and additionally on rotation around the predetermined axis.

According to the above-described positron CT scanner, an interval between each of the slice septa and its adjacent one substantially corresponds to a total of a plurality of detectors of a size in the direction of the predetermined axis. As a result, it is not necessary to thin the slice septa. Consequently with a numerical aperture of the detectors retained, oblique incidence of γ rays which is a cause of accidental coincidences can be prevented. Data acquisition is possible with efficient use of pair annihilations of electrons and positrons, and with improved S/N ratios. Furthermore, the slice septa are moved during a counting operation with respect to their associated detectors in the direction of the predetermined axis (central axis). Consequently the prevention of obliquely incident γ rays and each detecting efficiency of the detectors can be uniform among the respective detectors. The above-described functions make it possible to shorten a counting time and to improve its resolution power of the positron CT scanner.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art form this detailed description.

BRIEF DESCRIPTION OF THE DRAWING

FIG. 2 is a conceptual view of the entire positron CT scanner according to this invention.

FIG. 3A is view of the positron CT scanner according to a first embodiment of this invention explaining the structure and function.

FIG. 3B is a perspective view of slice septa according to the first embodiment of this invention.

FIG. 5A is view of the positron CT scanner according to a third embodiment of this invention explaining the structure and function.

FIG. 5B is a perspective view of slice septa according to the third embodiment of this invention.

FIG. 6A is view of the positron CT scanner according to a fourth embodiment of this invention explaining the structure and function.

FIG. 6B is a perspective view of slice septa according to the fourth embodiment of this invention.

FIG. 13A shows the result of the simulation about differential detection efficiencies in FIG. 12A. Structure of septa is shown in FIG. 11A and 12B, and the septa is in no motion.

FIG. 13B shows the result of the simulation about integral detection efficiencies in FIG. 12A. The structure of septa is shown in FIG. 11A and 12B, and the septa is in no motion.

FIG. 13C shows the result of the simulation about differential detection efficiencies in FIG. 12A. The structure of septa is shown in FIG. 11A and 12B, and an amplitude of a constant velocity motion is 20 mm.

FIG. 13D shows the result of the simulation about integral detection efficiencies in FIG. 12A. The structure of septa is shown in FIG. 11A and 12B, and the amplitude of the constant velocity piston motion is 20 mm.

FIG. 14A shows the result of the simulation about differential detection efficiencies in FIG. 12A. The structure of septa is shown in FIG. 11A and 12B, and an amplitude of a constant velocity motion is 22 mm.

FIG. 14B shows the result of the simulation about integral detection efficiencies in FIG. 12A. The structure of septa is shown in FIG. 11A and 12B, and the amplitude of the constant velocity piston motion is 22 mm.

FIG. 14C shows the result of the simulation about differential detection efficiencies in FIG. 12A. The structure of septa is shown in FIG. 11A and 12B, and the amplitude of the constant velocity motion is 24 mm.

FIG. 14D shows the result of the simulation about integral detection efficiencies in FIG. 12A. The structure of septa is shown in FIG. 11A and 12B, and the amplitude of the constant velocity piston motion is 24 mm.

FIG. 15A shows the result of the simulation about differential detection efficiencies in FIG. 12A. The structure of the septa is shown in FIG. 11A and 12B, and an amplitude of a sinusoidal motion is 16 mm.

FIG. 15B shows the result of the simulation about integral detection efficiencies in FIG. 12A. The structure of the septa is shown in FIG. 11A and 12B, and the amplitude of the sinusoidal piston motion is 16 mm.

FIG. 15C shows the result of the simulation about differential detection efficiencies in FIG. 12A. The structure of the septa is shown in FIG. 11A and 12B, and the amplitude of the sinusoidal motion is 18 mm.

FIG. 15D shows the result of the simulation about integral detection efficiencies in FIG. 12A. The structure of the septa is shown in FIG. 11A and 12B, and the amplitude of the sinusoidal piston motion is 18 mm.

FIG. 17A shows the best result of the simulation about differential detection efficiencies in the constant velocity piston motion of the parallel septa.

FIG. 17B shows the best result of the simulation about integral detection efficiencies in the constant velocity piston motion of the parallel septa.

FIG. 17C shows the best result of the simulation about differential detection efficiencies in the sinusoidal piston motion of the parallel septa.

FIG. 17D shows the best result of the simulation about integral detection efficiencies in the sinusoidal piston motion of the parallel septa.

FIG. 18 is explanatory views of the results of the simulation of FIGS. 11 and 12.

DESCRIPTION OF THE PREFERRED EMBODIMENTS

Figure 1:
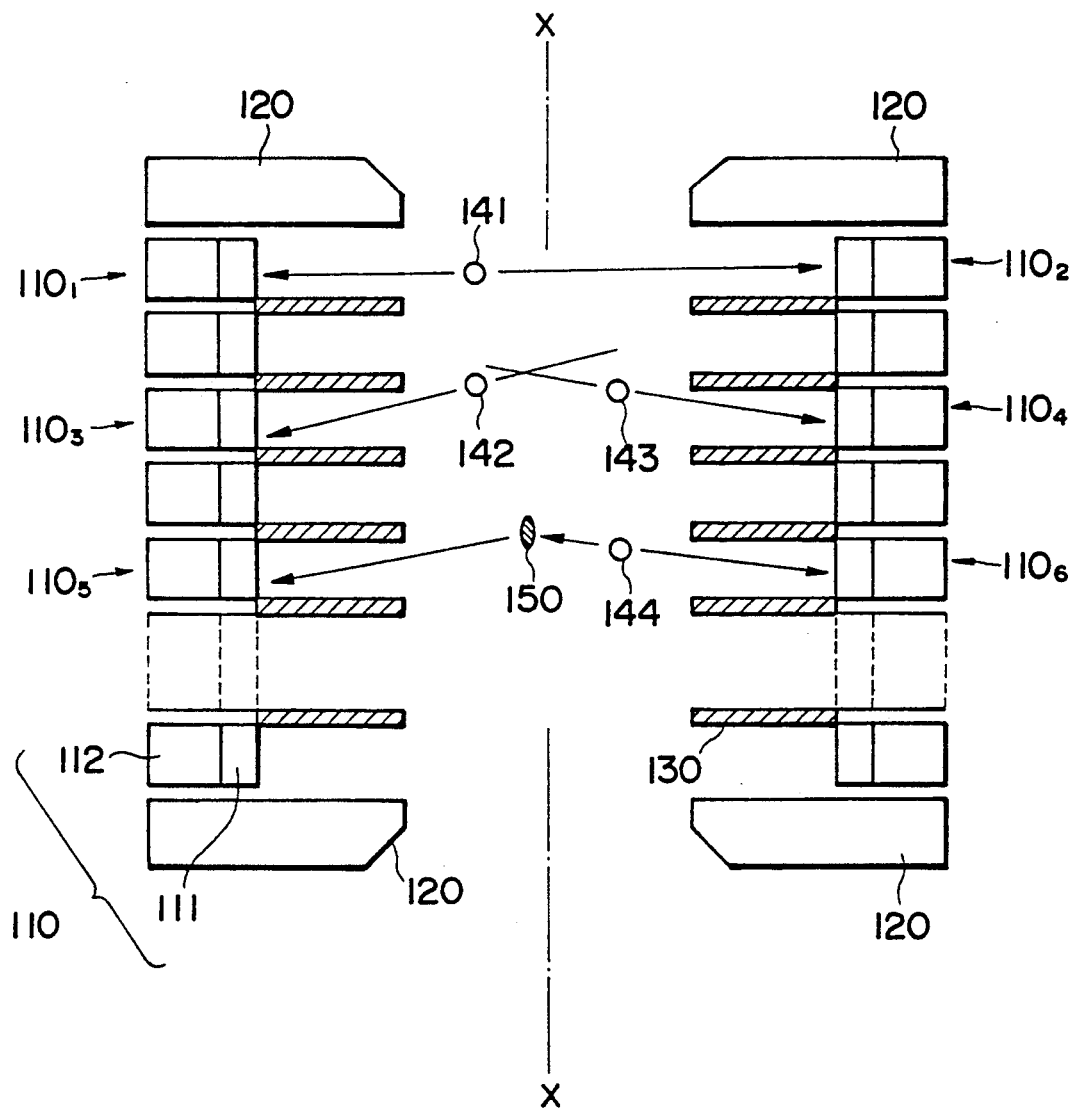
FIG. 1 is an explanatory view of the conventional positron CT scanner.

FIG. 2 is a conceptual view of the entire positron CT scanner according to this invention. This positron CT scanner comprises a photon detecting unit 100, a detected signal pre-processing unit 200, and an image restoring unit 300.

The photon detecting unit 100 comprises a number of detectors 110 arranged in multi-layers rings of which the outer shape is cylindrical; slice septa 130 for restricting detection fields of the respective detectors 110 so as to cross the central axis of the cylinder; and means 160 for driving the slice septa 130 in a piston (i.e., reciprocating) motion toward the central axis or in a rotary motion around the central axis.

The detected signal pre-processing unit 200 comprises the same number of discriminators 210 as the detectors each for analyzing an amplitude of an electric signal outputted by each of the detectors 110 (i.e., energy of an incident photon) and selecting candidates of expected event; a coincidence circuit for judging that only two photons have been generated in the associated layer, or two adjacent layers, based on the input of a signal of the candidate event selected by the discriminator 210, and informing the image restoring unit 300 of the occurrence of the event; and switches 230 controlled by the coincidence circuits 220 to operate, and provided for each of the outputs of the discriminators 210.

Two photons generated by a pair annihilation of a positron and an electron which has took place in an object-to-be-detected are detected separately as one individual photon by the photon detecting unit 100. These photons are judged to have been generated by a pair annihilation by the detected signal pre-processing unit 200, based on their energy and coincident generation. The image reconstructing unit 300 computes a position of the pair annihilation, based on data of the detectors 130 which have detected the photons as photon detection position information. The unit 300 statistically computes and processes a frequency of occurrences of pair annihilations near one position and presumes a material distribution inside the material-to-be-detected, and then restores this material distribution as an image and displays the image on an image display 320.

This invention is characterized by the photon detecting unit 100 of the above-described positron CT scanner, and uses the conventional art as the detected signal pre-processing unit 200 and the image restoring unit 300.

FIG. 3A and 3B are diagrammatic views of the positron CT scanner according to a first embodiment of this invention. FIG. 3A is a sectional view, and FIG. 3B is a perspective view of slice septa 130. In FIG. 3A and 3B, an interval between one of three slice septa 130 and its adjacent one is about 4 times a size of a $\gamma$ ray detector 110 in the direction of the central axis shown as X thereof, and the slice septa $130_1$–$130_3$ perform a piston-motion along the central axis at an amplitude corresponding to a size of about four detectors 110. In this embodiment, one $\gamma$ ray detector 110 comprised of scintillator 111 and photomultiplier 112 provides one detection cell.

In this embodiment, one sheet of slice septum $130_x$ is provided for 4 layers of $\gamma$ ray detectors 110. Even in the case that the $\gamma$ ray detector 110 is miniaturized, the slice septa 130 will not almostly lower the numerical aperture of the detectors. In other words, the slice septa 130 can be made the thicker, and the effect of their shielding $\gamma$ ray can be accordingly retained. The slice septa 130 are driven in a piston motion in the direction of the central axis, and the effect of the slice septa 130 shielding the oblique incidence of $\gamma$ rays, and the detection efficiency can be uniform among the respective $\gamma$ ray detectors. 110.

Figure 4B:
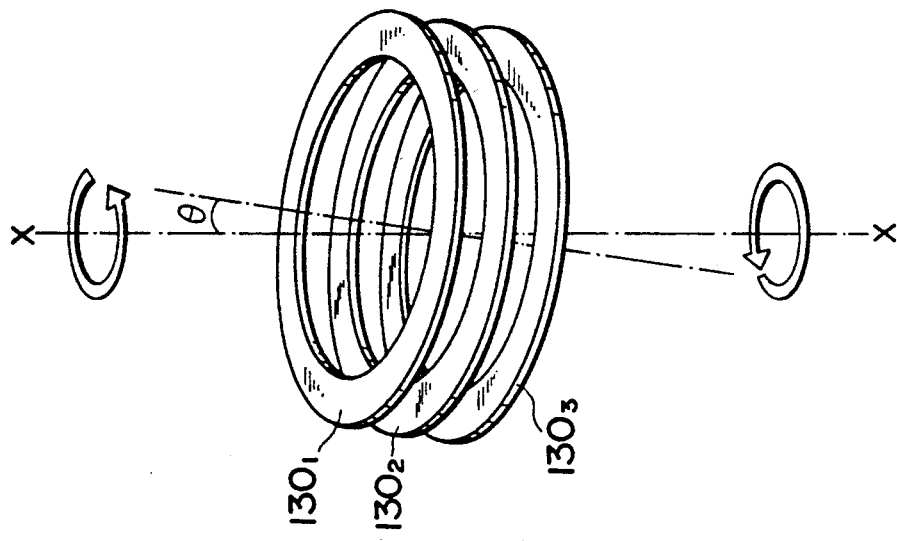
FIG. 4B is a perspective view of slice septa according to the second embodiment of this invention.
Figure 4A:
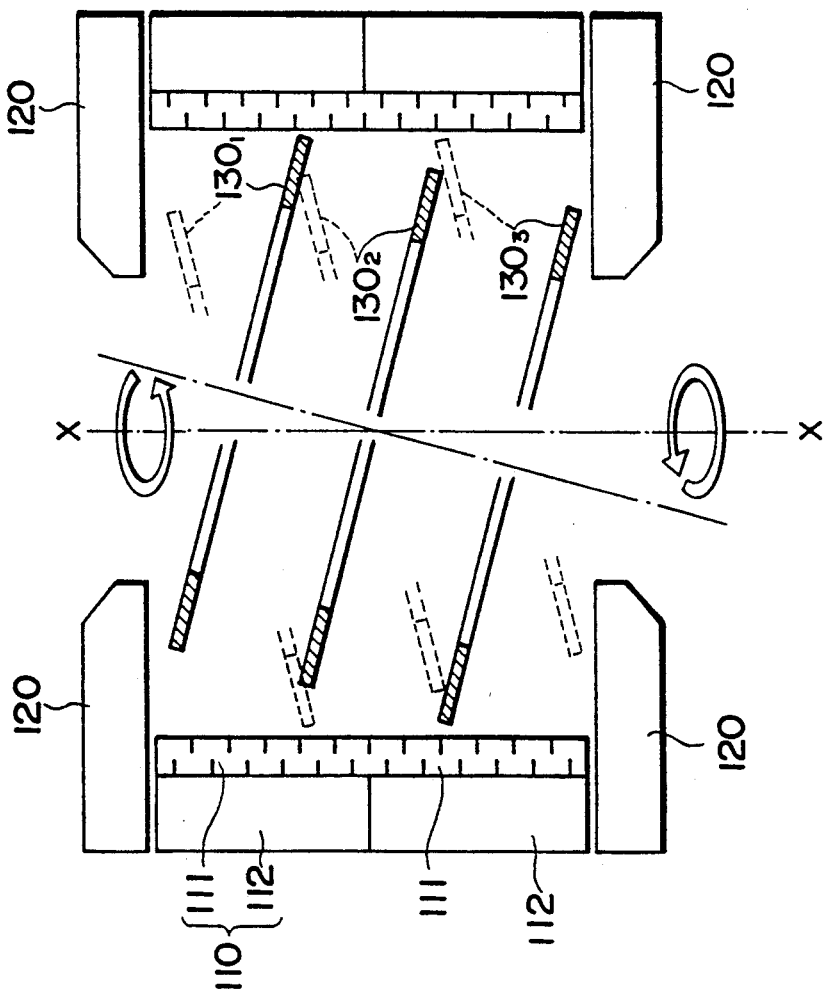
FIG. 4A is view of the positron CT scanner according to a second embodiment of this invention explaining the structure and function.

FIG. 4A and 4B are diagrammatic views of the positron CT scanner according to a second embodiment of this invention. In this embodiment, three slice septa $130_1$–$130_3$ are inclined at an angle $\theta$ to a central axis so as to perform a precession around the central axis shown as X. Equivalently in this arrangement as well, the slice septa 130 move with respect to their associated $\gamma$ ray detectors 110 in the direction of the central axis, and the same effects can be achieved as in the first embodiment. In this embodiment, one $\gamma$ ray detector 110 does not correspond to one detection cell. A scintillator 111 has a plurality of sections, and respective sections and respective elements of a photomultiplier 112 provide a plurality of detection cells. This photomultiplier 112 is exemplified by a multi-anode type photomultiplier.

FIG. 5A and 5B are diagrammatic views of the positron CT scanner according to a third embodiment of this invention. In this embodiment, three slice septa $130_1$–$130_3$ are parallel with one another but are not normal to a central axis, and additionally are rotatable about the central axis shown as X. In this case, the slice septa $130_1$–$130_3$ can make a piston or reciprocating type motion at an amplitude corresponding to a plurality of detection cells provided by γ ray detectors 110 relative to the detection cells. Accordingly the same effects as in the preceding embodiments can be produced. One detection cell may comprise one scintillator 111 and one photomultiplier as in the first embodiment, and otherwise one section of scintillator 111 and one element (picture element) of a multi-anode type photomultiplier 112 as in the second embodiment.

FIGS. 6A and 6B are diagrammatic views of the positron CT scanner according to a fourth embodiment of this invention. In this embodiment, slice septa 130 are provided in a helix and is rotatable about the central axis. When the slice septa 130 is rotated, they move relative to the respective detection cells in the direction of the central axis.

Figure 7B:
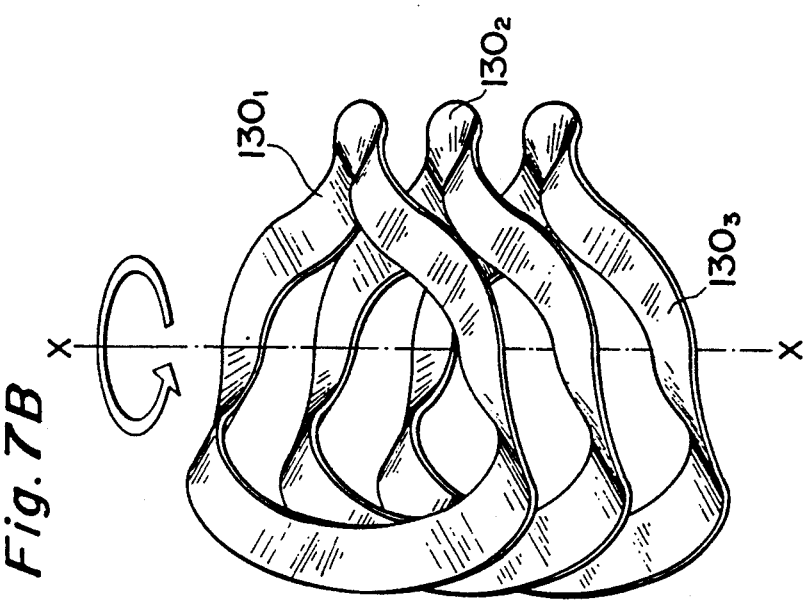
FIG. 7B is a perspective view of slice septa according to the fifth embodiment of this invention.
Figure 7A:
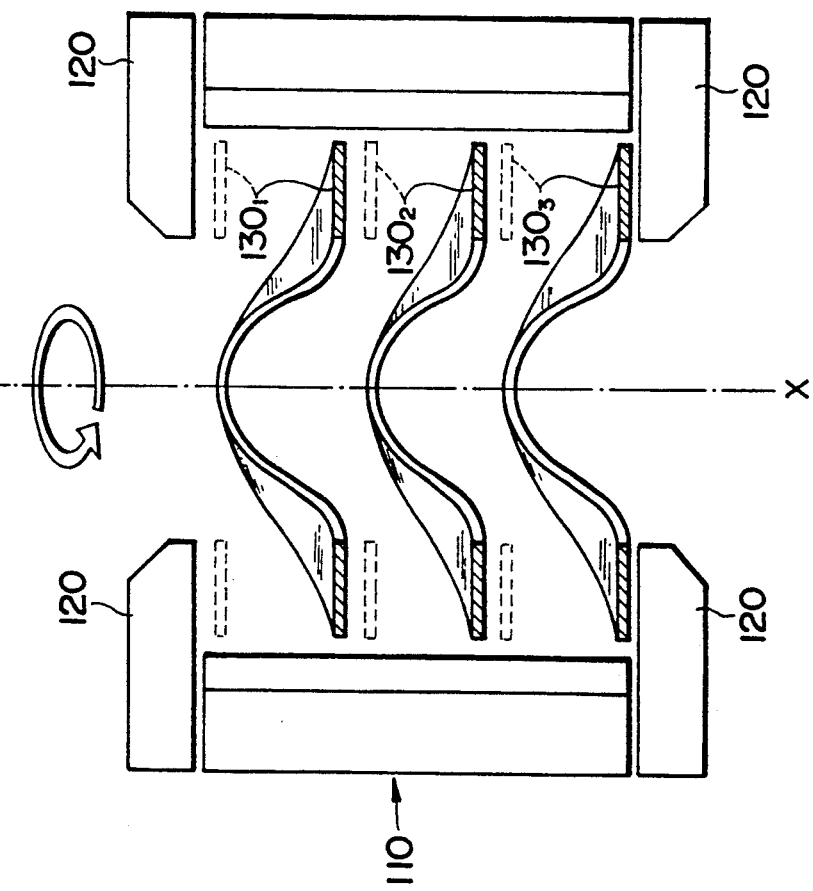
FIG. 7A is view of the positron CT scanner according to a fifth embodiment of this invention explaining the structure and function.

FIGS. 7A and 7B are diagrammatic views of the positron CT scanner according to a seventh embodiment of this invention. In this embodiment, annular slice septa 130 undulate in the direction of a central axis. By rotating the slice septa 130 about the central axis, the slice septa 130 are caused to make a piston motion with respect to respective detection cells. This embodiment is characterized in that the slice septa 130 can make a piston motion without reversing a rotational direction.

Figure 8B:
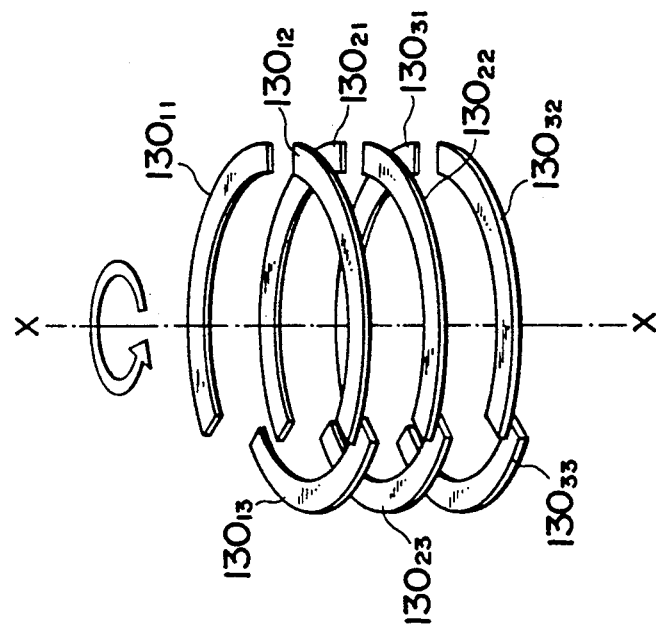
FIG. 8B is a perspective view of slice septa according to the sixth embodiment of this invention.
Figure 8A:
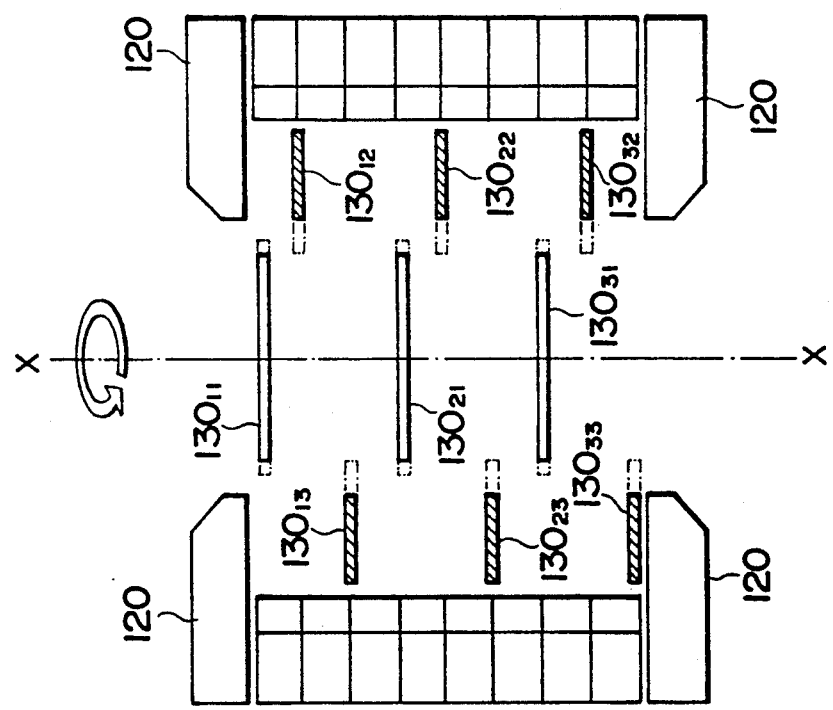
FIG. 8A is view of the positron CT scanner according to a sixth embodiment of this invention explaining the structure and function.

FIGS. 8A and 8B are diagrammatic views of the positron CT scanner according to a sixth embodiment of this invention. In this embodiment, each set of slice septa is provided in the form of sections of an annular plate $130_{11}$–$130_{13}$, $130_{21}$–$130_{23}$, $130_{31}$–$130_{33}$. Positions of the slice septa 130 in the direction of a central axis can be displaced by steps by rotating the slice septa 130. In this embodiment, the slice septa 130 do not continuously move, as they do in the first to the fifth embodiments, but the effects intended by this invention can be sufficiently produced. Especially it can be equivalent to the case that one slice septum is provided between each of detection cells and its adjacent one to make an interval between each of three sets of slice septa $130_{11}$–$130_{13}$, $130_{21}$–$130_{23}$, $130_{31}$–$130_{33}$ and its adjacent set correspond to three detector cells.

Next, means for driving the slice septa will be explained. The drive mode of the slice septa includes piston motions in the direction of the central axis, and rotary motions around the central axis.

Figure 9:
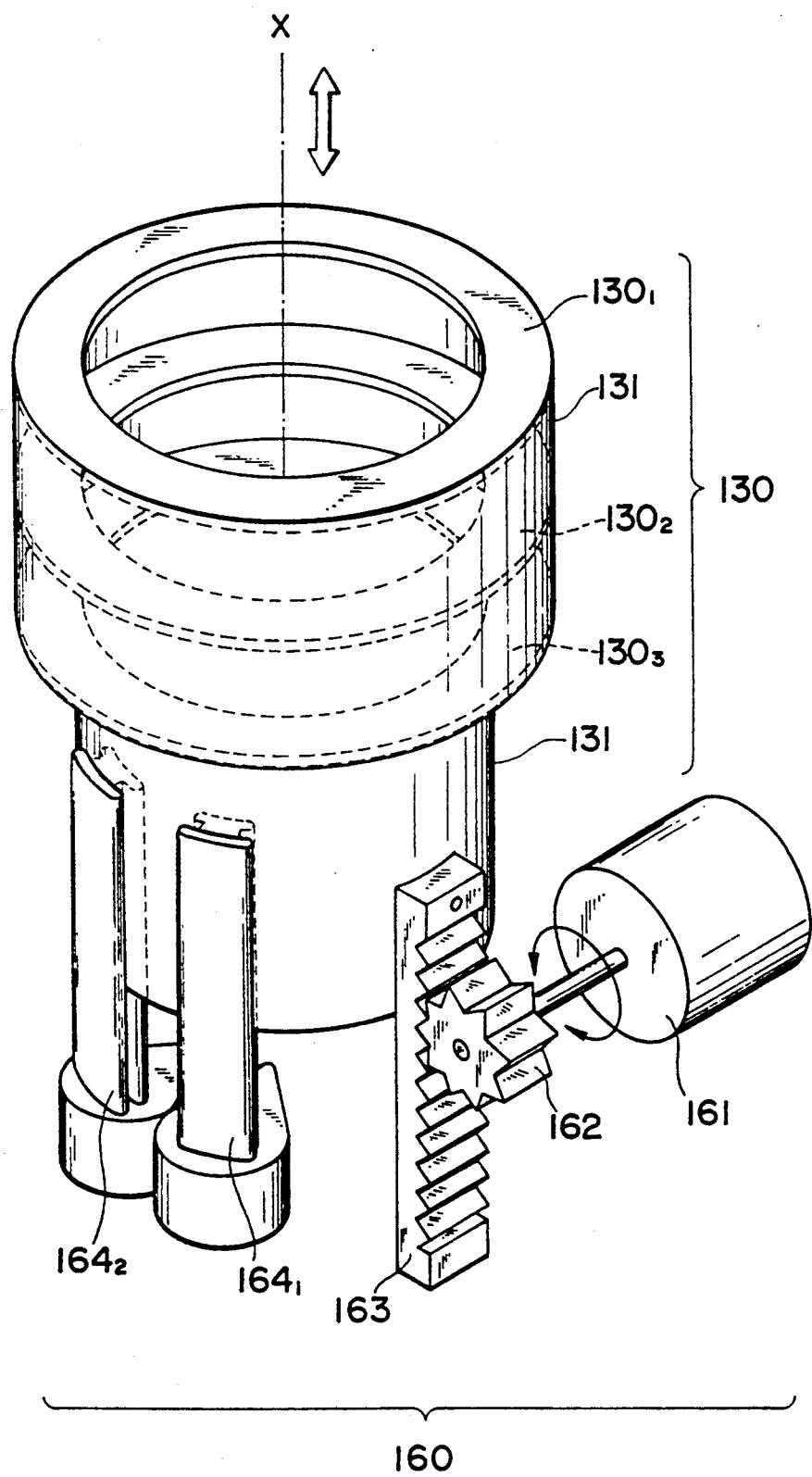
FIG. 9 is a view of an example of the means for driving the slice septa (piston motions) involved in the first embodiment.

FIG. 9 shows one example of driving means for the piston motions. The slice septa 130 comprise a plurality of annular plate members $130_1$–$130_3$, and a holder 131. The holder 131 is mechanically connected to a driving unit 160. The driving unit 160 comprises a driving motor 161, a gear 162, a pinion gear 163, and a guide rail 164. The driving motor 161 is rotated to drive all the slice septa 130 to make a piston motion in the direction of the central axis.

Figure 10:
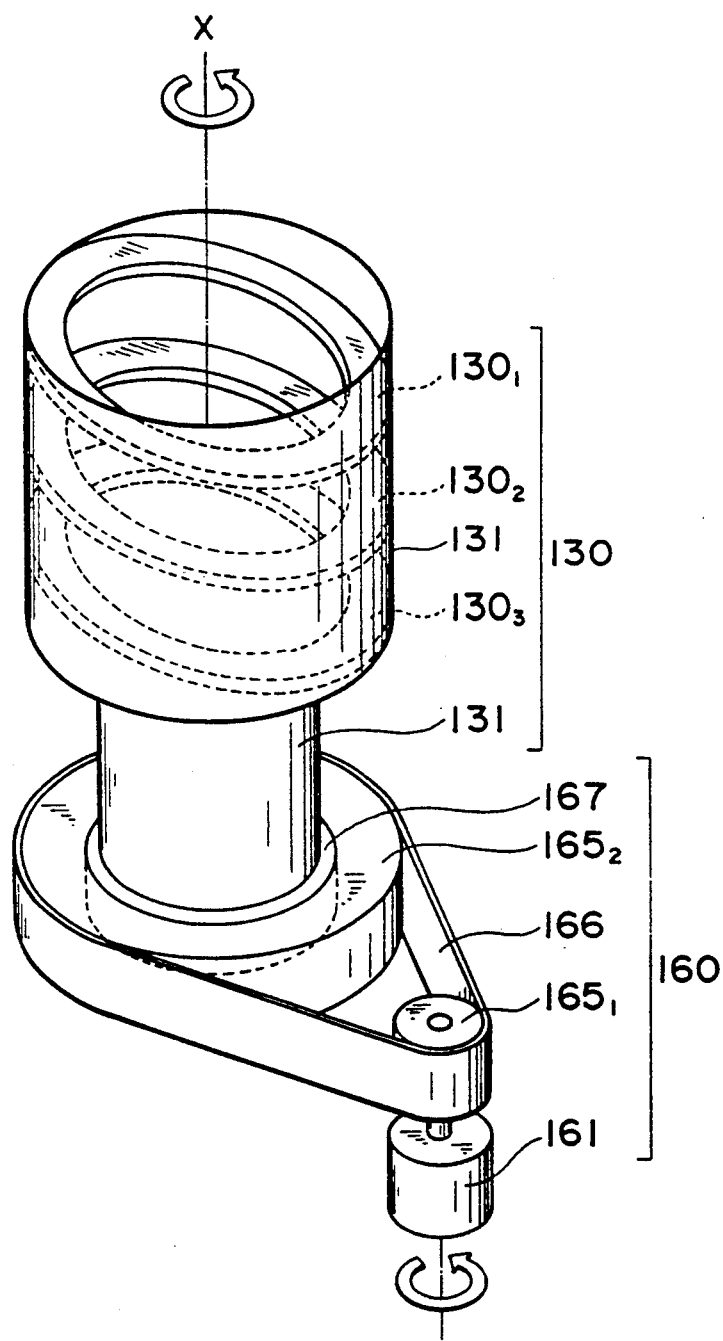
FIG. 10 is a view of an example of the means for driving slice septa (rotary motions) involved in the second to the sixth embodiments.

FIG. 10 shows one example of means for driving means for the rotary motions. The slice septa 130 comprise a plurality of annular plate members $130_1$–$130_3$, and a holder 131. The holder is mechanically connected to a driving unit 160. The driving unit 160 comprises a driving motor 161, a pulley 165, a belt 166 and a bearing gear 167. The driving motor 161 is rotated to drive all the slice septa 130 to make a rotary motion around the central axis. This example has been explained in connection with the drive of the third embodiment described above, but can drive the other embodiments which make rotary motions.

Figure 11A:
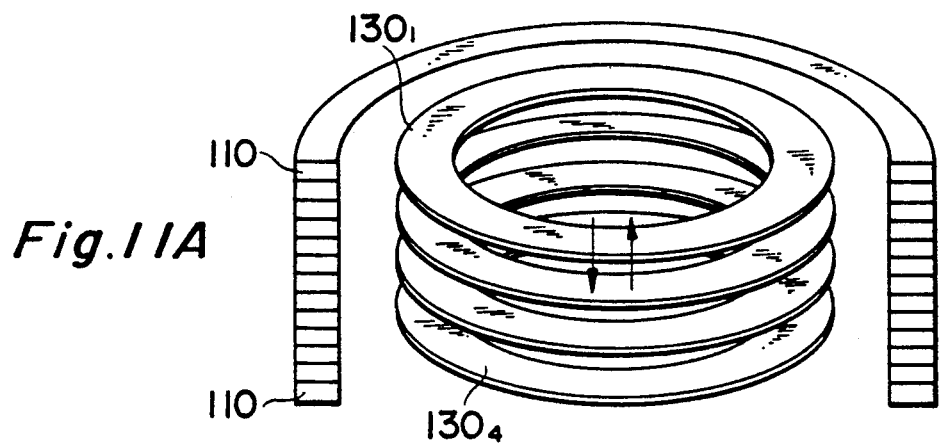
FIG. 11A is a view of a piston motion of slice septa according to this invention.
Figure 11B:
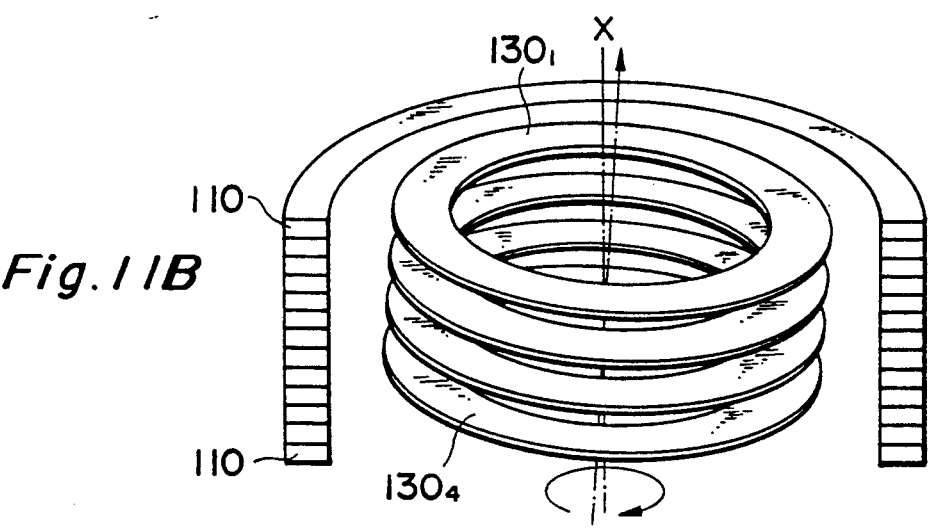
FIG. 11B is a view of a precession motion of slice septa according to this invention.
Figure 11C:
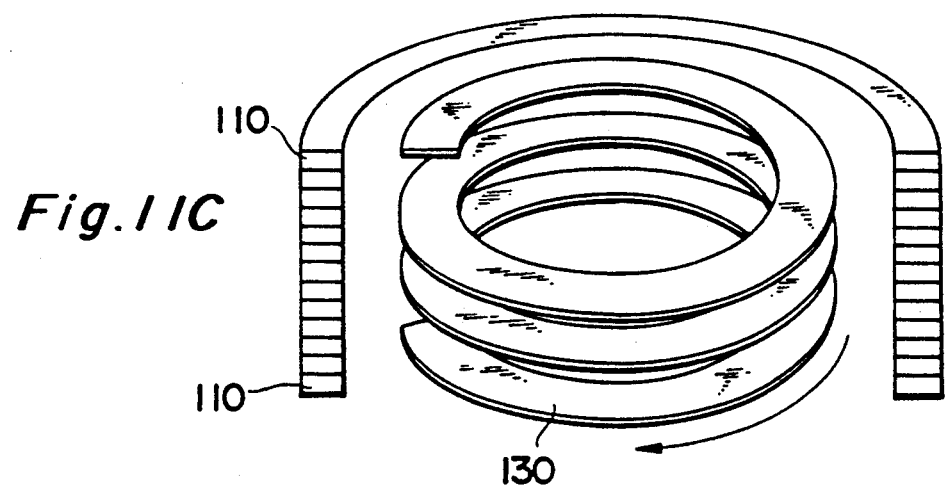
FIG. 11C is a view of a spiral rotary motion of slice septa according to this invention.
Figure 12A:
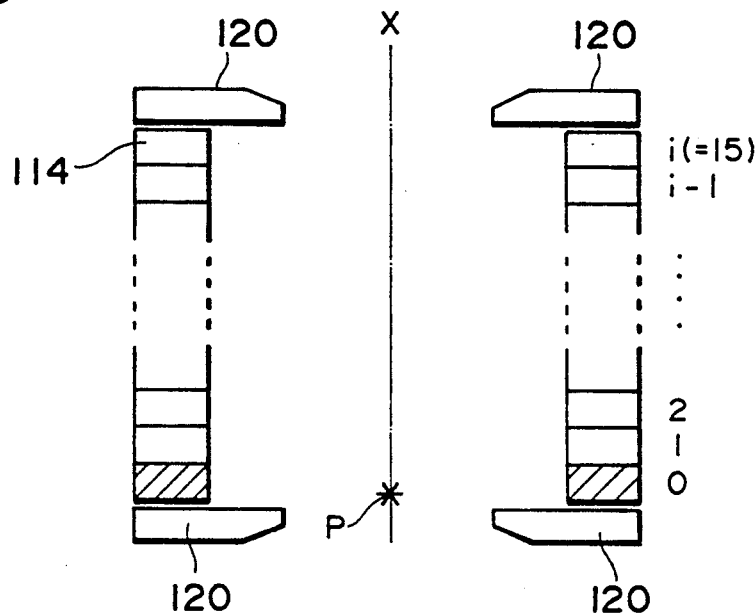
FIG. 12A is a view of a layer structure of the detectors of a simulation of the positron CT scanner according to this invention.
Figure 12B:
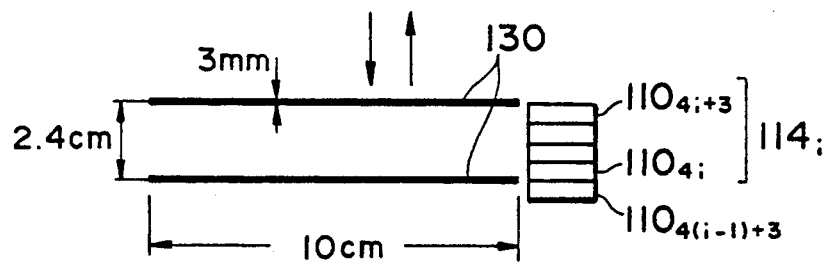
FIG. 12B is a view of one structure of the slice septa in the simulation.
Figure 12C:
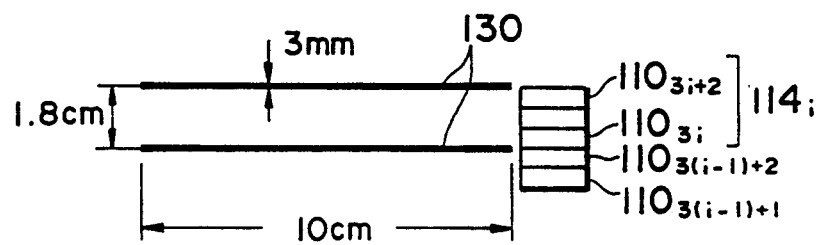
FIG. 12C is a view of another structure of the slice septa in the simulation.
Figure 16A:
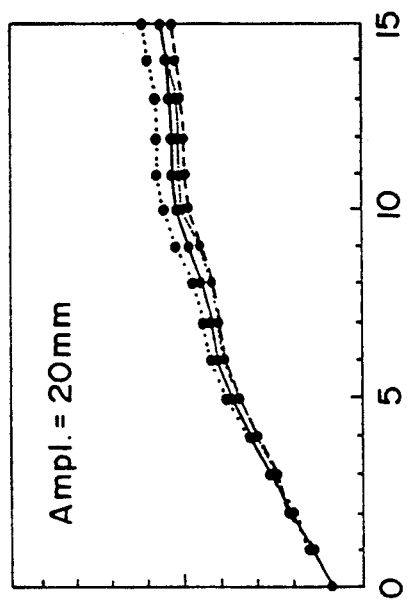
FIG. 16A shows the result of the simulation about differential detection efficiencies in FIG. 12A. The structure of the septa is shown in FIG. 11A and 12B, and an amplitude of a sinusoidal motion is 22 mm.
Figure 16B:
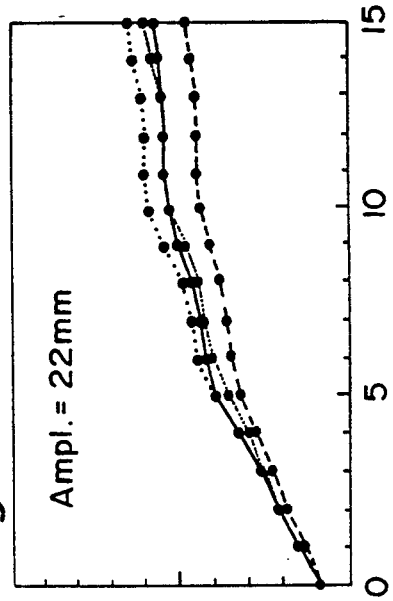
FIG. 16B shows the result of the simulation about integral detection efficiencies in FIG. 12A. The structure of the septa is shown in FIG. 11A and 12B, and the amplitude of the sinusoidal piston motion is 22 mm.
Figure 16C:
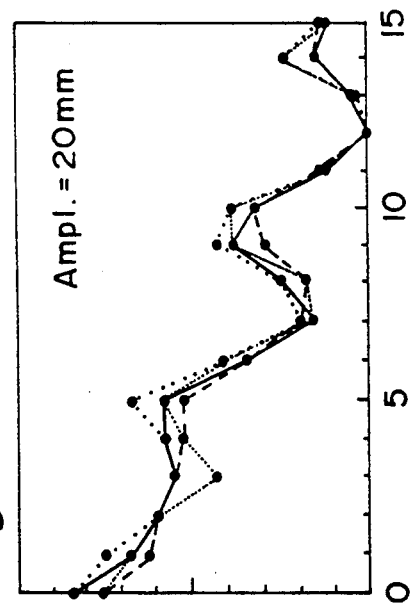
FIG. 16C shows the result of the simulation about differential detection efficiencies in FIG. 12A. The structure of the septa is shown in FIG. 11A and 12B, and the amplitude of a sinusoidal motion is 24 mm.
Figure 16D:
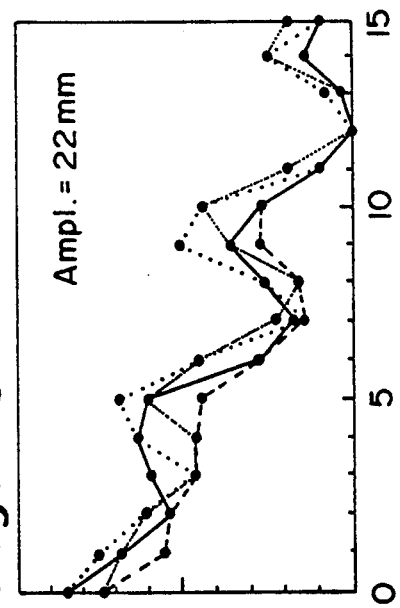
FIG. 16D shows the result of the simulation about integral detection efficiencies in FIG. 12A. The structure of the septa is shown in FIG. 11A and 12B, and the amplitude of the sinusoidal piston motion is 24 mm.
Figure 18A:
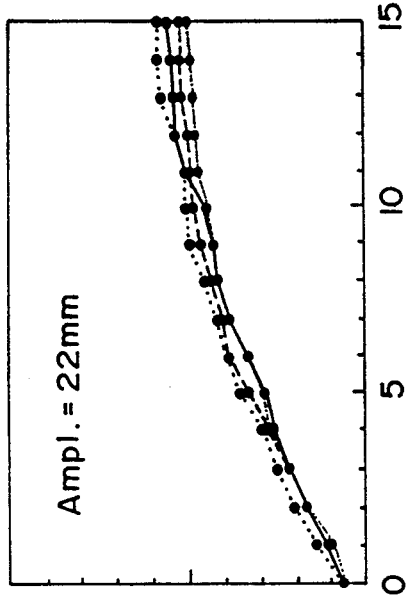
FIG. 18A shows the best result of the simulation about differential detection efficiencies in a precession of the parallel septa.
Figure 18B:
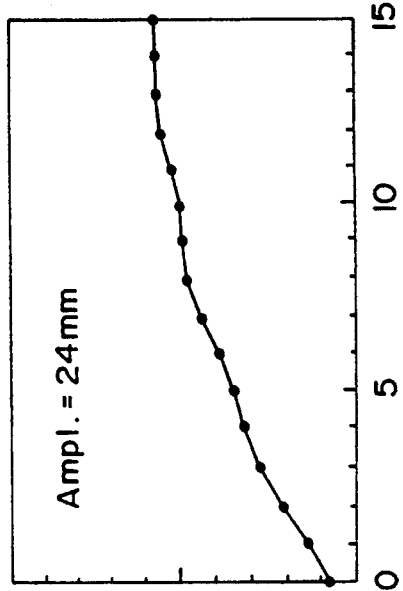
FIG. 18B shows the best result of the simulation about integral detection efficiencies in the precession of the parallel septa.
Figure 18C:
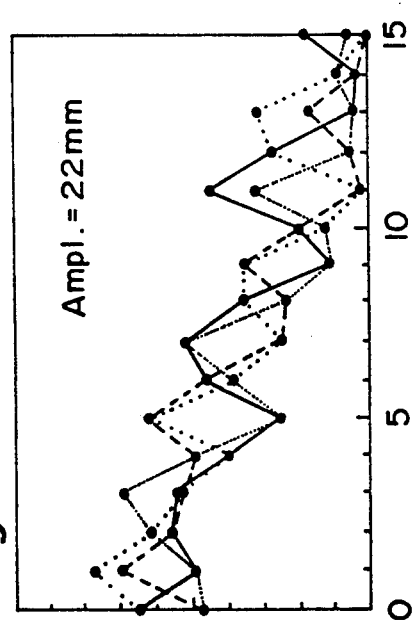
FIG. 18C shows the best result of the simulation about differential detection efficiencies in a rotary motion of a helical septum.
Figure 18D:
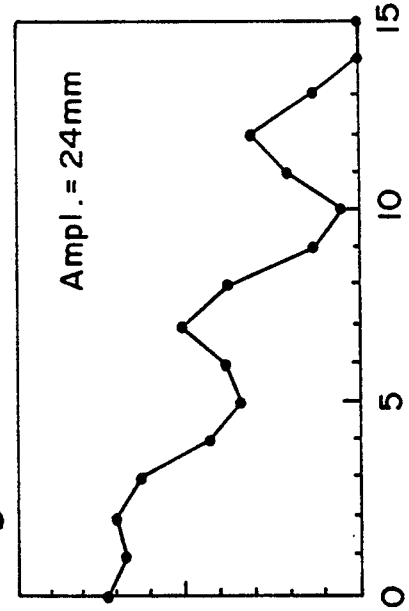
FIG. 18D shows the best result of the simulation about integral detection efficiencies in the rotary motion of the helical septum.

FIGS. 11A to 11C show modes of the drive of the slice spectra 130. A first drive mode is a piston motion and is shown in FIG. 11A. A second drive mode is a sinusoidal piston motion and is shown also in FIG. 11A. A third drive mode is an axis swaying drive, i.e., a precession and is shown in FIG. 11B. A fourth drive mode is a spiral rotary motion and is shown in FIG. 11C. As shown in FIG. 12A, the layer structure of γ ray detectors includes 16 layers (i=0–15), and a ratio of a γ-ray detectors arranging pitch vs. an interval between slice septa 130 is 4 as shown in FIG. 12B.

The results are shown in FIGS. 13A to 18D. In FIGS. 13A to 18D, the numbers 0 to 15 on the horizontal axis indicate the numbers of the opposed groups of γ ray detectors 114 (refer to FIG. 12A). The drawings (Dif) on the left side show detection sensitivities of the respective opposed γ ray detectors, and the drawings (Int) on the right side show integrated values of the detection sensitivities of the 0-th to i-th detectors. In the respective drawings, the four curves correspond to four γ ray detectors within one interval between slice septa. In the drawings showing the integrated values on the right side, cases in which the four curves better conform to one another have better characteristics.

FIGS. 13A to 14D show in contrast cases of the constant velocity piston motion as in FIG. 11A and of no motion. FIGS. 13A and 13B show the case of no motion (amplitude: 0 mm), and FIGS. 13C and 13D show the case of the piston motion at an amplitude of 20 mm. FIGS. 14A and 14B show the cases of the piston motion at an amplitude of 22 mm, and FIGS. 14C and 14D show the cases of the piston motion at an amplitude of 24 mm. It is seen that the best characteristics can be obtained when an amplitude, and an interval of the slice septa 130 agree with each other.

FIGS. 15A to 16D show cases of the sinusoidal piston motions respectively at amplitudes of 16, 18, 22, 24 mm. It is seen that in these cases the best characteristics can be obtained when the slice septa 130 are moved in the sinusoidal piston motion at an amplitude corresponding to about 75% of an interval of the slice septa 130.

FIGS. 17A to 18D show in contrast characteristics of the respective drive modes at amplitude conditions producing the best results.

From the invention thus described, it will be obvious that the invention may be varied in many ways. Such variations are not to be regarded as a departure from the spirit and scope of the invention, and all such modifications as would be obvious to one skilled in the art are intended to be included within the scope of the following claims.

We claim:
1. A positron CT scanner comprising:
   a plurality of detectors arranged in multi-layer rings about a predetermined central axis, each detector having at least one detecting cell;
   slice septa comprising a plurality of annular members formed about a non-parallel axis relative to the central axis, the annular members axially spaced along the non-parallel axis to define inter-member intervals along the non-parallel axis; and
   means for moving said slice septa during image detection about the central axis to cause the inter-septa intervals to move relative to said detecting cells.
2. A positron CT scanner according to claim 1, wherein said means for moving moves the slice septa in a rotary motion about the predetermined central axis.

3. A positron CT scanner according to claim 1, wherein
each detector comprises one scintillator and one photodetector and provides one detecting cell.

4. A positron CT scanner according to claim 1, wherein
each detector comprises a scintillator divided into a plurality of sections and one photodetector.

5. A positron CT scanner according to claim 4, wherein
the photodetector includes means for detecting incident photons.

6. A positron CT scanner according to claim 1, further comprising means for processing output signals of the detectors and providing a sectional image of a detected object.

7. A positron CT scanner comprising:
a plurality of detectors arranged in multi-layer rings about a predetermined central axis, each detector having at least one detecting cell;
slice septa comprising a plurality of septa for restricting the detection fields of the detectors so that the detection fields intersect the predetermined axis by an interval in the direction of the predetermined axis corresponding to a selected number of the detecting cells; and
means for driving the slice septa in a first direction along the predetermined axis and the opposite direction along the predetermined axis during a detection operation to cause the septa to move relative to the detecting cells.

8. A positron CT scanner according to claim 7, wherein the septa are spaced a selected distance along the predetermined axis.

9. A positron CT scanner according to claim 8, wherein the slice septa comprise a plurality of annular disk members formed about a central axis that is coincident with the predetermined axis, and a holder for retaining a relative positional relationship of the members.

10. A positron CT scanner according to claim 9, wherein the driving means drives the slice septa in a reciprocating piston motion along the direction of the predetermined axis.

11. A positron CT scanner according to claim 7, wherein each detector comprises one scintillator and one photodetector and provides one detecting cell.

12. A positron CT scanner according to claim 11, wherein each detecting cell comprises means for converting a detected incident photon into an electric signal corresponding to the energy thereof.

13. A positron CT scanner according to claim 7, wherein each detector comprises a scintillator divided into a plurality of sections and one photodetector.

14. A positron CT scanner according to claim 13, wherein the photodetector includes means for determining incident photons.

15. A positron CT scanner according to claim 13, wherein each detecting cell comprises means for converting a detected incident photon into an electric signal corresponding to the energy thereof.

16. A positron CT scanner according to claim 7, further comprising means for processing the output signals of the detectors to provide a sectional image of a detected object.

17. A positron CT scanner comprising:
a plurality of detectors arranged in multi-layer rings about a predetermined central axis, each detector having at least one detecting cell;
slice septa comprising a plurality of annular members concentric with the predetermined axis and aligned non-normal to the predetermined axis, and a holder for retaining a relative positional relationship with the detectors, said slice septa restricting detection fields of the detectors so that the detection fields intersect the predetermined axis by an interval in the direction of the predetermined axis corresponding to a plural number of the detecting cells; and
means for driving the slice septa in a first direction and the opposite direction along the predetermined axis during a detection operation, to cause the septa to move relative to the detecting cells.

18. A positron CT scanner according to claim 17, wherein the driving means drives the slice septa in a rotary motion around the predetermined axis.

19. A positron CT scanner according to claim 18, wherein the photodetector includes means for detecting incident photons.

20. A positron CT scanner according to claim 17, wherein each detector comprises one scintillator and one photodetector and provides one detecting cell.

21. A positron CT scanner according to claim 20, wherein each detecting cell comprises means for converting a detected incident photon into an electric signal corresponding to the energy thereof.

22. A positron CT scanner according to claim 17, wherein each detector comprises a scintillator divided into a plurality of sections and one photodetector.

23. A positron CT scanner according to claim 22, wherein each detecting cell comprises means for converting a detected incident photon into an electric signal corresponding to the energy thereof.

24. A positron CT scanner comprising:
a plurality of detectors arranged in multi-layer rings about a predetermined central axis, each detector having at least one detecting cell;
slice septa comprising a single helical plate member advancing in the direction of the predetermined axis, and a holder of the member, for restricting detection fields of the detectors so that the detection fields intersect the predetermined axis by an interval in the direction of the predetermined axis corresponding to a plural number of the detecting cells; and
means for driving the slice septa in a first direction and the opposite direction along the predetermined axis during a detection operation, to cause the septa to move relative to the detecting cells.

25. A positron CT scanner according to claim 24, wherein the driving means drives the slice septa in a rotary motion around the predetermined axis.

26. A positron CT scanner according to claim 24, wherein each detector comprises one scintillator and one photodetector and provides one detecting cell.

27. A positron CT scanner according to claim 26, wherein each detecting cell comprises means for converting a detected incident photon into an electric signal corresponding to the energy thereof.

28. A positron CT scanner according to claim 24, wherein each detector comprises a scintillator divided into a plurality of sections and one photodetector.

29. A positron CT scanner according to claim 28, wherein each detecting cell comprises means for converting a detected incident photon into an electric signal corresponding to the energy thereof.

30. A positron CT scanner according to claim 24, wherein the photodetector includes means for detecting incident photons.

31. A positron CT scanner comprising:
a plurality of detectors arranged in multi-layer rings about a predetermined central axis, each detector having at least one detecting cell;
slice septa means comprising a plurality of annular members axially spaced in the direction of the predetermined axis, and a holder for retaining a relative positional relationship with detectors, said slice septa means for restricting detection fields of the detectors so that the detection fields intersect the predetermined axis by an interval in the direction of the predetermined axis corresponding to a plural number of the detecting cells; and
means for driving the slice septa means during image detection in a first direction and the opposite direction along the predetermined axis to cause the septa means to move relative to the detecting cells.

32. A positron CT scanner according to claim 31, wherein the driving means drives the slice septa means in a rotary motion around the predetermined axis.

33. A positron CT scanner according to claim 31, wherein each detector comprises one scintillator and one photodetector and provides one detecting cell.

34. A positron CT scanner according to claim 33, wherein each detecting cell comprises means for converting a detected incident photon into an electric signal corresponding to the energy thereof.

35. A positron CT scanner according to claim 31, wherein each detector comprises a scintillator divided into a plurality of sections and one photodetector.

36. A positron CT scanner according to claim 35, wherein the photodetector includes means for detecting incident photons.

37. A positron CT scanner according to claim 35, wherein each detecting cell comprises means for converting a detected incident photon into an electric signal corresponding to the energy thereof.

38. A positron CT scanner comprising:
a plurality of detectors arranged in multi-layer rings about a predetermined central axis, each detector having at least one detecting cell;
slice septa comprising a plurality of curved sectors, each curved sector being offset with respect to one another in the direction of the predetermined axis, and a holder for retaining a relative positional relationship thereof with the detectors, the slice septa for restricting detection fields of the detectors so that the detection fields intersect the predetermined axis by an interval in the direction of the predetermined axis corresponding to a plural number of the detecting cells; and
means for driving the slice septa in a first direction and the opposite direction along the predetermined axis during a detection operation, to cause the septa to move relative to the detecting cells.

39. A positron CT scanner according to claim 38, wherein the driving means drives the slice septa in a rotary motion around the predetermined axis.

40. A positron CT scanner according to claim 39, wherein the photodetector includes means for detecting incident photons.

41. A positron CT scanner according to claim 39, wherein each detecting cell comprises means for converting a detected incident photon into an electric signal corresponding to the energy thereof.

42. A positron CT scanner according to claim 38, wherein each detector comprises one scintillator and one photodetector and provides one detecting cell.

43. A positron CT scanner according to claim 38, wherein each detector comprises a scintillator divided into a plurality of sections and one photodetector.

44. A positron CT scanner according to claim 43, wherein each detecting cell comprises means for converting a detected incident photon into an electric signal corresponding to the energy thereof.

45. A positron CT scanner comprising:
a plurality of detectors arranged in multi-layer rings about a predetermined central axis, each detector having a detection field in the direction of the predetermined central axis and having at least one detecting cell for detecting incident energy from positron-electron annihilations from an object within the detection field of a respective detector;
means for defining a plurality of field-of-view intervals along the predetermined central axis for restricting the detection fields of the detectors along the predetermined central axis; and
means for moving the first-mentioned means during detection so that said field-of-view intervals are moved in a first direction along the predetermined axis and in the opposite direction along the predetermined axis to cause the field-of-view intervals to move relative to the detectors in the first direction and then in the opposite direction along the predetermined axis.

46. A positron CT scanner according to claim 45, wherein said means for moving comprises means for reciprocating said first-mentioned means along said predetermined central axis.

47. A positron CT scanner according to claim 45, wherein said means for moving comprises means for rotating said first-mentioned means relative to said predetermined central axis.

48. A positron CT scanner according to claim 45, wherein said first-mentioned means comprises a plurality of annular rings axially spaced along and aligned normal to the predetermined central axis, the field-of-view intervals defined between said annular rings.

49. A positron CT scanner according to claim 45, wherein said first-mentioned means comprises a plurality of annular rings axially spaced along and aligned normal to a second axis that is not parallel to the predetermined central axis, the field-of-view intervals defined between said annular rings.

50. A positron CT scanner according to claim 45, wherein first-mentioned means comprises a plurality of annular rings axially spaced along and aligned non-normal to the predetermined central axis, the field-of-view intervals defined between said annular rings.

51. A positron CT scanner according to claim 45, wherein said first-mentioned means comprises a continuous helix member extending along the predetermined central axis, the field-of-view intervals defined between adjacent portions of the helix.

52. A positron CT scanner according to claim 45, wherein said first-mentioned means comprises a plurality of undulating rings axially spaced along and aligned normal to the predetermined central axis, the field-of-view intervals defined between adjacent sections of said undulating rings.

53. A positron CT scanner according to claim 45, wherein said first-mentioned means comprises a plurality of curved sectors axially spaced along and aligned normal to the predetermined central axis, the field-of-view intervals defined between adjacent sections of said curved sectors.

* * * * *